United States Patent [19]

Lansiart et al.

[11] 4,103,677

[45] Aug. 1, 1978

[54] ULTRASONIC CAMERA

[75] Inventors: Alain Lansiart, Gif; Jean-Claude Gaucher, Versailles; Jean Lequais, St. Remy les Chevreuse; Jean-Luc Moretti, St-Maur; Annick Quettier, Creteil, all of France

[73] Assignee: Commissariat a l'Energie Atomique, Paris, France

[21] Appl. No.: 742,234

[22] Filed: Nov. 16, 1976

[30] Foreign Application Priority Data

Nov. 24, 1975 [FR] France .................................. 75 35817

[51] Int. Cl.² ............................................ A61B 10/00
[52] U.S. Cl. ..................................... 128/2 V; 73/621; 73/625
[58] Field of Search ........................... 128/2 V, 2.05 Z; 73/67.8 S, 67.9, 67.7, 620, 621, 625, 626; 340/1 R

[56] References Cited

U.S. PATENT DOCUMENTS

| 3,480,002 | 11/1969 | Flaherty et al. | 128/2 V |
|---|---|---|---|
| 3,587,561 | 6/1971 | Ziedonis | 128/2.05 Z |
| 3,693,415 | 9/1972 | Whittington | 73/67.8 S |
| 3,881,466 | 5/1975 | Wilcox | 128/2 V |
| 3,938,502 | 2/1976 | Bom | 128/2 V |

FOREIGN PATENT DOCUMENTS 2,507,177  9/1975  Fed. Rep. of Germany .......... 128/2 V

*Primary Examiner*—Kyle L. Howell
*Attorney, Agent, or Firm*—Lane, Aitken, Dunner & Ziems

[57] ABSTRACT

The camera comprises an emitting section and a receiving section which are both located on the surface of a portion of a cylinder. The receiving section consists of juxtaposed and parallel strips located in the central part of the portion of cylinder. The emitting section consists of two groups each constituted by a band of parallel strips which is placed on each side of the receiving section. Each emitter is constituted by a pair of strips having parallel sides each forming part of a directrix of the cylinder. Electronic means are provided for exciting the different emitting strips and collecting the signals received by the different receiving strips.

9 Claims, 5 Drawing Figures

ULTRASONIC CAMERA

This invention relates to an ultrasonic camera which is capable of producing ultrasonic images of parts of the human body at a sufficiently high rate to reproduce the physiological movements of the parts under observation.

It is known that diagnosis by means of ultrasonic waves is a highly effective means for observing organs consisting of soft tissues which do not have the characteristic qualities of absorption for separating them by means of X-rays.

The image is formed by directing an ultrasonic wave beam onto an organ and by detecting the ultrasonic echos by means of receivers in order to determine the shape and structure of the affected organ.

The ultrasonic camera in accordance with the invention is designed for medical applications in which it has proved necessary to carry out dynamic observations for the purpose of following the progressive variation of an organ during its movement. The response times of the order of magnitude of the time phenomena occurring in human organs are typically of the order of one second.

One of the requisite conditions to be satisfied by an ultrasonic camera for medical use is imposed at the level of the ultrasonic power received by the patient which must have the lowest possible value. In fact, in order to carry out dynamic observations, it appears necessary to expose the patient to a high flux of ultrasonic waves.

The ultrasonic camera in accordance with the invention permits medical diagnoses at a sufficiently high rate to permit observation of motion of human organs with a low value of ultrasonic power.

In all visual display systems, the image of the object to be observed is obtained point by point on the screen of a cathode-ray tube. It is therefore only necessary to observe the object point by point while concentrating the ultrasonic energy only over a small field of observation corresponding to the point which is visualized. This field undergoes displacement in order to sweep the entire surface to be scanned.

The ultrasonic camera in accordance with the invention makes it possible to achieve this objective. The camera essentially comprises an emitting section and a receiving section which are both located on the surface of a portion of cylinder. The cylindrical structure of the emission surface makes it possible to concentrate the rays along a focal line segment corresponding to the emitters which are excited. The receiving section of the ultrasonic camera is constituted by a plurality of *n* receiving elements in the form of strips disposed in parallel relation, said receiving elements being placed side by side and located substantially in the central part of the portion of cylinder of the camera. The emitting section of the camera in accordance with the invention is constituted by a plurality of *m* emitters which are also in the form of parallel strips, said strips being disposed in two groups, each group being constituted by a band of parallel strips and the two bands being located on each side of the receiving section. Each emitter is constituted by at least one pair of strips, the parallel sides of each of the two emitting strips being such as to form part of a directrix of said cylinder in order to ensure good concentration of the ultrasonic energy on the focal line segment which coincides substantially with the axis of the cylinder, the length of the segment being such as to correspond to the length of the emitting portion of cylinder, that is, to the number and to the length of the emitting strips. In accordance with the invention, the ultrasonic camera further comprises electronic means for exciting the different emitting strips at uniform time intervals and electronic means for collecting the signals received by the different receiving strips.

In the stationary position, the portion of cylinder in accordance with the invention makes it possible to scan the surface of the body along a line by exciting the different groups of emitters one after the other. In order to scan an entire surface along a first plane corresponding to a frontal section of the organ under observation (known as observation in the C mode), it is necessary to impart an oscillating movement to the portion of a cylinder, for example about a central generating-line which passes substantially through the center of the receiving strips. The camera in accordance with one embodiment of the invention comprises electro-mechanical means for subjecting said portion of cylinder to a movement of angular oscillation about said central generating-line. The amplitude can be reduced if necessary in order to observe a smaller field at a higher rate.

It is also possible to observe the organ under study along a sagittal section, that is to say in a plane which passes through a generating-line of the cylinder, by scanning a line with successive emissions from the different emitters and by collecting on the receiving strips the signals which are re-emitted by the different points of said line, then by resuming the operation after having displaced the cylinder in translational motion over a given interval or pitch at right angles to the generating-lines. In ultrasonic diagnosis terminology, this type of observation is usually designated as observation in the B mode. In this type of operation, the camera in accordance with the invention includes means for displacing the cylinder in translational motion.

As can readily be understood, it is possible to combine between two line scans a movement of rotation and a movement of translation in order to observe the organ along a section having an adjustable angle of slope between the frontal section and the sagittal section. It is also possible to visualize frontal lines in accordance with the A mode.

Finally, it is possible to employ the camera in accordance with the invention in the time-motion (TM) mode. In this case, the same line is scanned at uniform time intervals and the time-dependent variation of the signals reemitted by this line of the organ can be observed. Electronic means of known type make it possible to superimpose these different images of the line on an oscilloscope screen. These means are not described in detail since they are well known to anyone versed in the art.

In order to optimize the reception of signals in a preferential embodiment of the invention, the receiving strips are assembled in the case of each group of emitters along the Fresnel zones corresponding to the emitting point of the scanned line, the ultrasonic waves emitted by or reflected from said point being such as to arrive in phase in these different receivers, thus permitting excellent reception of the signal.

Further properties and advantages of the invention will become more readily apparent from the following description of one exemplified embodiment which is given by way of explanation and not in any limiting sense, reference being made to the accompanying drawings, wherein.

Figure 1:
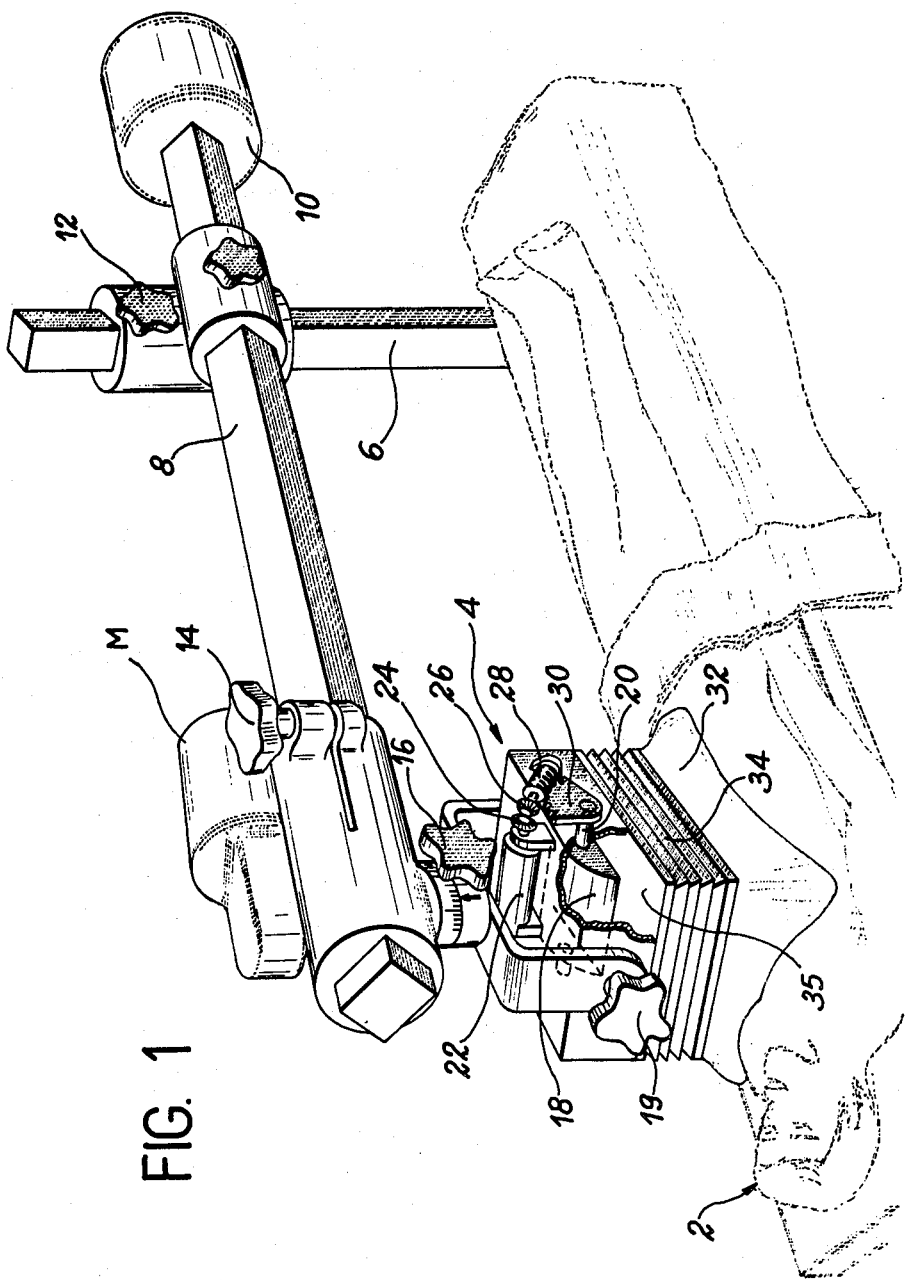
FIG. 1 is a diagram of an ultrasonic camera in accordance with the invention for the observation of a patient.

FIG. 1 shows the utilization diagram of an ultrasonic camera in accordance with the invention, this camera being employed for producing an image of parts of the human body. The patient 2 as shown in the horizontal position in FIG. 1 is observed by the ultrasonic camera which is equipped with a mechanical scanning unit as designated by the general reference 4. A system comprising arms 6 and 8, a balance-weight 10 and clamping screws 12, 14, 16 and 19 serves to displace and to lock the ultrasonic camera in position in order to observe different parts of the body. The weight of the camera is not supported by the patient but by the frame. The mechanical portion of the camera is capable of displacement in rotational motion about a vertical axis; the clamping screw 16 serves to secure the camera against rotation about said axis and to lock this latter in a stationary position; similarly the clamping screw 14 serves to fix the position of the camera in horizontal translation. The cylinder 18 is capable of displacement in oscillating motion about a spindle 20 under the action of a mechanism which serves to scan a zone in the frontal plane as mentioned earlier. Said mechanism comprises a motor 22 which drives a pinion 24 and this latter in turn drives a bevel pinion 26 which is set at 90°, said pinion 26 being rigidly fixed to a worm-screw 28 which drives the toothed wheel 30 in a movement of rotation. The spindle of the cylinder 18 is rigidly fixed to the toothed wheel 30, with the result that the cylinder is capable of pivotal motion about a central axis which is constituted by the spindle 20 and which passes substantially through the center of the receiving strips as shown in detail in FIG. 2. An electric control device for a motor of known type makes it possible to reverse the direction of rotation of said motor in order to impart an oscillating movement of rotation to the cylinder.

A contact is established between the mechanical unit of the camera and the patient by means of a flexible bag 32, a bellows element 34 being provided for withdrawing or advancing the camera body with respect to the patient and thus adjusting the depth of the plane of observation. A polyethylene plate 35 eliminates mechanical vibrations caused by the oscillations of the camera body.

In order to form sagittal sections along a plane which passes through a generating-line of the cylinder, a motor M serves to displace the cylinder in translational motion.

Figure 2:
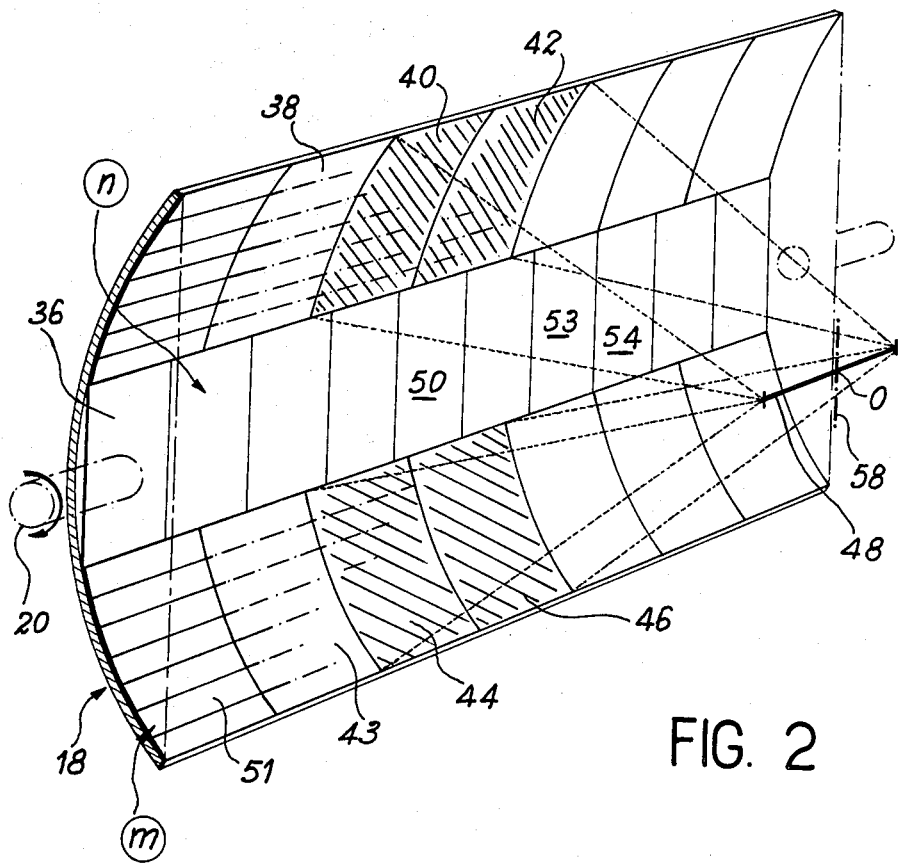
FIG. 2 is a diagram of a portion of a cylinder comprising the emitting and receiving sections of the ultrasonic camera, the dimensions of said sections as given solely by way of example being 0.22 × 0.15 meter.

FIG. 2 shows in detail the cylinder 18 which comprises the emitting and receiving elements. At the time of scanning of a zone, said cylinder oscillates about the central axis 20. In the example shown in FIG. 2, the emitting strips such as the strip 38 are excited by doublet. For example, the strips 40 and 42 are excited simultaneously and the same clearly occurs in the case of the strips 43, 44 and 46 in order to direct a substantially focused beam of ultrasonic waves along the straight-line segment 48. The focusing segment 48 coincides substantially with the axis of the cylinder.

The strips for receiving the ultrasonic wave are located in the central portion of the cylinder between the two bands of emitting strips. The waves reflected from the body to be studied are returned towards said receiving strips in order to be detected thereon. As will hereinafter become apparent with reference to FIG. 3, a certain number of receivers such as for example the receivers 50, 53, 54 and so forth are opened in phase in order to optimize the reception of the signal. By virtue of the geometry of the receiving strips, these latter receive waves in phase in respect of emitters located on the line 58 which is illuminated only in the vicinity of the point O, with the result that the portion of the body observed is the portion which surrounds the point O. It is readily apparent that, in order to scan a line, that is to say a straight line constituted by a series of linear segments such as the segment 48, the different groups of emitters are excited at regular intervals of time; in this embodiment, the $m$ emitters are excited by doublet one after the other.

The emitting elements are constituted by strips such as those designated by the reference 38 which are in turn constituted by small elements such as those designated by the reference 51 and having a substantially rectangular shape. By way of example, said elements can have a width of 1 cm and a length of 1.3 cm and are bonded to the support 18 of cylindrical shape and of insulating material. The ratio between the dimensions of these elements and the wavelength of the ultrasonic waves employed makes it possible to assimilate the concave polygonal surface obtained with a cylindrical surface. The sound emission is of the scialytic illumination type which prevents cast shadows, thus making it possible to detect a detail which is partly concealed.

Figure 3:
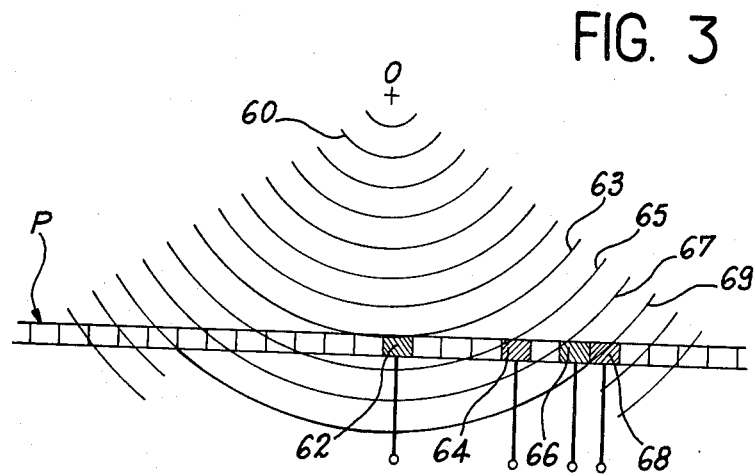
FIG. 3 is a diagram showing the association of the different receivers as a function of the Fresnel zones corresponding to a point of observation on the focal line of concentration corresponding to a given group of emitters.

In FIG. 3, there is shown a view which illustrates the structure for receiving the signal on the receiving strips. FIG. 3 is a diagrammatic view corresponding to a cross-section of the device along the plane P which passes through the point O and the axis 20. The center of emission O in the case of the reflected waves transmits ultrasonic waves having substantially spherical wave surfaces such as those represented in cross-section at 60. The various receivers 62, 64, 66 and 68 receive waves in phase or in other words correspond substantially to the Fresnel zones in which the different waves are in phase; these receivers are located at the intersections of the plane of the receivers P with the equidistant circles such as those designated by the references 63, 65, 67 and 69. At a given instant, the receivers of this assembly are opened, with the result that all the signals transmitted are in phase and originate from one and the same point. It is readily apparent that, at the time of scanning of line and subsequently at the time of scanning of the surface, the emitters change position as well as the point O, with the result that the different receiving strips which are opened in phase correspond to different assemblies. The detail of the configurations and localization of the Fresnel zones are well known to those who are versed in the art.

Figure 4:
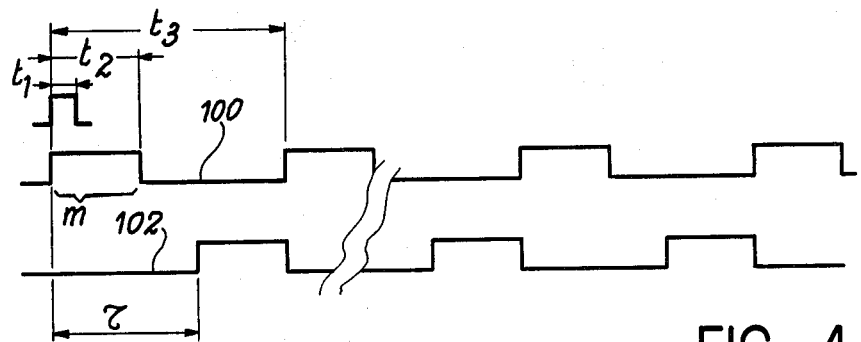
FIG. 4 is a time diagram of the electrical excitations of the emitters and receivers which are synchronized in time.

FIG. 4 shows the time diagram of the excitations of the emitters and the receivers. The $m$ different groups of emitters are excited one after the other by electrical oscillations at frequencies of the order of several Mc/s (1 to 4 Mc/s, for example) and during a time interval $t_1$ as represented on curve 100. The time interval $t_2 = mt_1$ corresponding to the scanning of one line is of the order of one hundred microseconds, for example 150 microseconds. Since the radius of the cylindrical surface is of the order of 25 cm, the waves take approximately 330 microseconds to travel from an emitter to the object and to return to the receiver. Synchronization of the reception is represented on curve 102; the time interval $\tau$ which elapses between the emission and the reception corresponds to a return trip of the wave between object and emitter-receiver ($\tau$ being 330 microseconds in this precise case). The receiving time is substantially equal to the emission time of each sequence. The time interval $t_3$ which elapses between two scans of any one line is longer than the time interval $\tau$: it corresponds to the time interval which elapses between two successive excitations of any one emitter. In one example of construction, this time interval $t_3$ is of the order of 500 microseconds. After the time interval $t_2$ corresponding to scansion of one line, the cylinder 18 (shown in FIG. 2) has rotated through a predetermined angle $\theta$ and a further line is then scanned.

This mode of operation demonstrates the fact that it is not necessary to apply ultrasonic waves to the entire line during the scanning period. The number of adjacent emitters which are excited simultaneously can be variable and is usually of the order of several units.

The picture-taking rate is sufficient to follow for example the pulsatory movement of organs and can be 16 images per second, for example, over the entire field being scanned.

Figure 5:
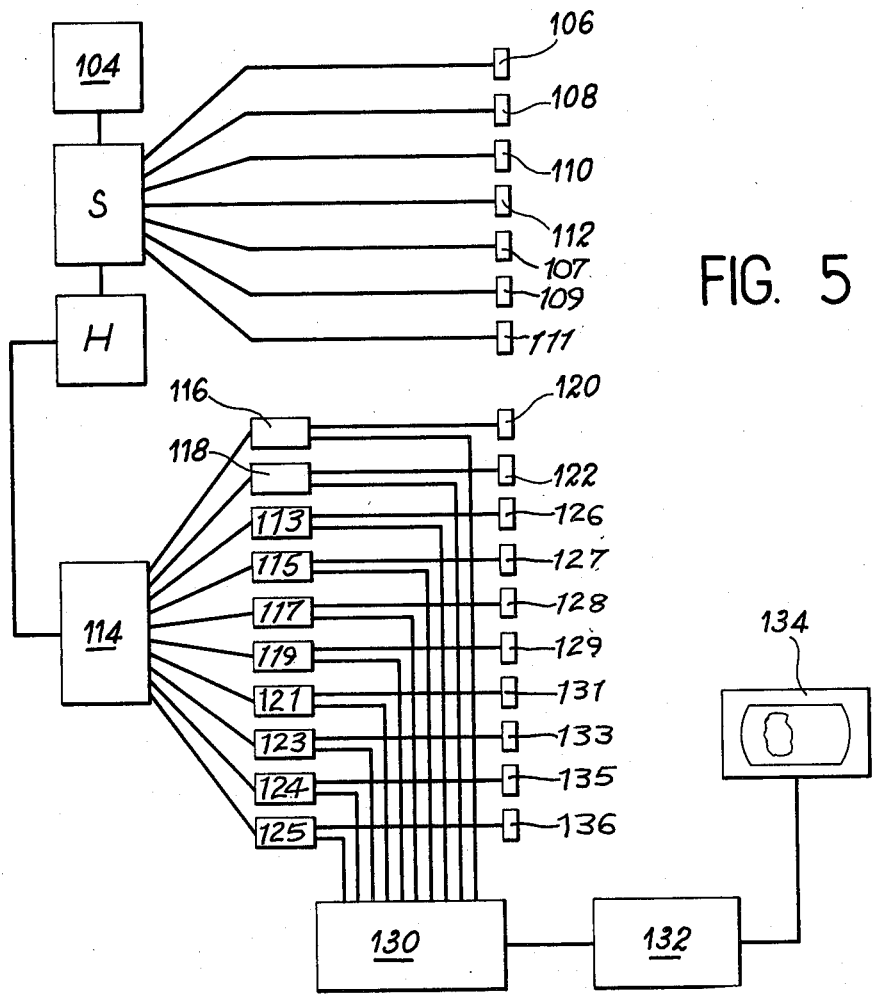
FIG. 5 is a diagram of the various electronic elements of the camera.

In FIG. 5, there is shown the electronic diagram of the different means for exciting the emitters and collecting the signal received on the receiving strips. An oscillator 104 sends electric waves at a frequency of 2 to 4 Mc/s (waves corresponding to ultrasonic waves) into a selector S which is synchronized by a clock H for delivering electric signals such as those shown at 100 in FIG. 4; the electric signals are transmitted to grouped ultrasonic emitters such as those designated by the references 106, 108 and 110 during a time interval $t_1$ (FIG. 4); the clock H makes it possible to scan the entire series of emitters in synchronism with the selector and the second emission excites the emitters 107, 108, 109, 110, 111 and 112. After a time interval $t_3 > t_2 = mt_1$, a shift register contained in the same selector S then permits a further scan corresponding to a new line. The signals derived from the clock H are also fed into a delay unit such as 114 which transmits the signals represented at 102 in FIG. 4 to gates such as 116, 118, 113, 115, 117, 119, 121, 123, 124, and 125 so forth which are connected to receivers such as 120, 122, 126, 127, 128, 129, 131, 133, 135 and 136. In respect of a given time interval, the "selecting" delay line 114 opens a certain number of gates corresponding to Fresnel zones of an emission point of the object.

In other words, under the influence of the selectors contained in the unit 114, the different Fresnel zone corresponding to a point of the line and coinciding with predetermined detectors are put into communication with an adderamplifier 130 as a result of the opening of gates such as 116, 118 and the like. After addition, there is obtained a total received signal corresponding to a point of the line which is fed into a converter 132 in order to carry out the scanning of a television set 134.

It is readily apparent that the electronic devices as shown diagrammatically in the figure and briefly described in the foregoing are already known and that the construction of such devices is within the capacity of anyone versed in the art.

What we claim is:

1. An ultrasonic camera comprising an emitting section and a receiving section which are both located on the inner surface of a portion of a cyliner, the receiving section being constituted by a plurality of n receiving elements in the form of strips disposed in parallel relation and the emitting section being constituted by a plurality of m emitters which are also in the form of parallel strips, the strips of the emitter are disposed in two groups, each group being constituted by a band of parallel strips and the two bands being located on each side of the receiving section, each emitter being constituted by a pair of strips, the parallel side of each of the two emitting strips being such as to form part of a directrix of said cylinder, the ultrasonic camera being further provided with electronic means for exciting the different emitting strips with the same phase and electronic means for collecting the signals received by the different receiving strips.

2. A camera according to claim 1, wherein said camera comprises electromechanical means for displacing said cylinder in a movement of translation at right angles to the generating-lines of the cylinder.

3. A camera according to claim 1, wherein said camera comprises electromechanical means for imparting a movement of angular oscillation to said portion of cylinder comprising an emitting and receiving section about an axis in substantially coincident relation with the generating-line of the portion of cylinder which passes through the center of the emitting strips.

4. A camera according to claim 1, wherein said electronic means for exciting the different emitting strips with the same phase are constituted also for exciting sequentially groups of p adjacent emitters, each excitation being such as to extend over a time interval $t_1$ and the successive excitations of the same emitter being separate by the time interval $t_3$ which is longer than the time interval $t_2 = mt_1$.

5. An ultrasonic camera according to claim 1, wherein the electronic means for collecting the signals received by the different receiving strips comprise:
   gates each associated with a strip;
   a clock H for delivering a square-wave electrical signal of constant value during a time interval having a length $t_1$, a single square wave of said signal which opens the g gates associated with the g strips in coincident relation with the g Fresnel zone being such as to correspond to the reflection of the ultrasonic waves produced by a group of p adjacent emitting strips and the following square wave of said signal which opens the following g gates being such as to correspond to the following group of emitting strips p.

6. An ultrasonic camera according to claim 5, wherein said camera further comprises electronic means for sequentially exciting all the g gates by means of the clock H at time intervals separated by the interval $t_3$ corresponding to a translational displacement of the cylinder over a predetermined distance of travel in a direction at right angles to the generating-lines of said cylinder.

7. An ultrasonic camera according to claim 5, wherein said camera further comprises electronic means for sequentially exciting all the groups of g gates by means of the clock H at time intervals separated by the interval $t_3$ during which the portion of cylinder has rotated through angles $\theta$, $2\theta$, $3\theta$ and so forth.

8. An ultrasonic camera according to claim 5, wherein said camera comprises an adder for adding the signals emitted by the different groups of g gates, a scanning converter fed by said adders, the output of said converter being connected to a visual display screen.

9. an ultrasonic camera according to claim 1, wherein each emitting strip is constituted by a plurality of adjacent rectangular elements which are excited simultaneously.

* * * * *